US006626358B1

(12) United States Patent
Breimesser et al.

(10) Patent No.: US 6,626,358 B1
(45) Date of Patent: Sep. 30, 2003

(54) POCKET MONITOR FOR PATIENT CARDS

(75) Inventors: Fritz Breimesser, Nuremberg (DE); Arno Reitz, Pullach (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/525,375

(22) Filed: Mar. 15, 2000

(30) Foreign Application Priority Data

Mar. 15, 1999 (DE) .......................................... 199 11 416

(51) Int. Cl.⁷ ................................................. G06K 5/00
(52) U.S. Cl. ........................................ 235/380; 368/10
(58) Field of Search .............................. 235/380, 382, 235/472.01, 472.02, 486; 705/2, 3; 368/10, 107–109, 111

(56) References Cited

U.S. PATENT DOCUMENTS

| 4,258,354 A |   | 3/1981  | Carmon et al. ......... 340/309.4 |
|-------------|---|---------|----------------------------------|
| 4,695,954 A |   | 9/1987  | Rose et al. ................... 221/5 |
| 5,002,062 A | * | 3/1991  | Suzuki |
| 5,099,463 A | * | 3/1992  | Lloyd et al. .................. 368/10 |
| 5,157,640 A | * | 10/1992 | Backner ....................... 368/10 |
| 5,239,166 A |   | 8/1993  | Graves |
| 5,408,443 A | * | 4/1995  | Weinberger |
| 5,691,932 A | * | 11/1997 | Reiner et al. ................. 368/10 |
| 6,012,636 A | * | 1/2000  | Smith |
| 6,032,085 A | * | 2/2000  | Laurent et al. |
| 6,082,622 A | * | 7/2000  | Hartmann et al. |
| 6,198,695 B1 | * | 3/2001 | Kirton et al. |
| 6,209,011 B1 | * | 3/2001 | Vong et al. ................. 708/112 |
| 6,304,797 B1 | * | 10/2001 | Shusterman |
| 6,314,384 B1 | * | 11/2001 | Goetz |
| 6,314,405 B1 | * | 11/2001 | Richardson .................... 705/3 |
| 6,397,190 B1 | * | 5/2002 | Goetz ............................ 705/3 |
| 6,421,650 B1 | * | 7/2002 | Goetz et al. ................... 705/3 |

FOREIGN PATENT DOCUMENTS

| DE | 195 36 204 |   | 1/1997  |
|----|------------|---|---------|
| EP | 0 575 256  | * | 12/1993 |
| JP | 05-220221  | * | 8/1993  |
| JP | 08-256994  | * | 10/1996 |

* cited by examiner

*Primary Examiner*—Diane I. Lee
(74) *Attorney, Agent, or Firm*—Schiff Hardin & Waite

(57) ABSTRACT

A device for monitoring medication and treatment of patients using a patient card on which the patient's attending physician stores all relevant findings, diagnoses and treatment steps, is in the form of a pocket monitor having a clock or DCF receiver, a plug-in receptacle for the patient card and a reader for the treatment-relevant data as well as a display screen for displaying the readout information relating to the type and time of the upcoming treatments and/or medications.

10 Claims, 1 Drawing Sheet

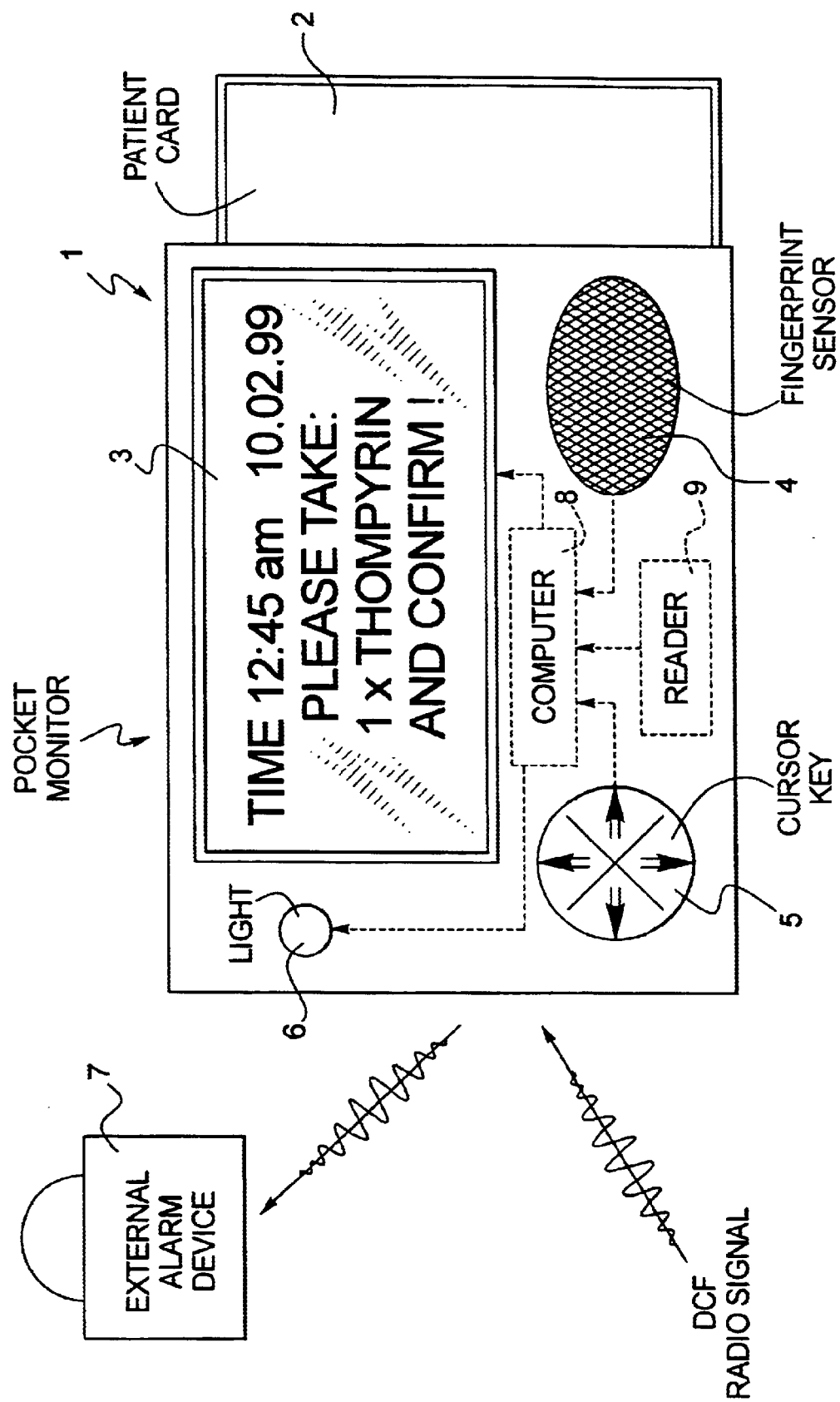

POCKET MONITOR FOR PATIENT CARDS

BACKGROUND OF THE INVENTION

1. Field of the Invention

The present invention is directed to a device for monitoring the medication and treatment of patients using a patient card, on which the patient's attending physician stores all relevant findings, diagnoses und treatment steps.

2. Description of the Prior Art

Recently, so-called patient cards have been introduced to a great extent. All essential findings, diagnoses and treatment steps in addition to the patient's personal data and health insurance coverage are stored thereon. This not only facilitates insurance invoicing, but also allows the entire medical history of a patient to be accessible to the attending physician in order to be able to deduce the appropriate treatment steps in each case. For the individual patient, however, this patient card has only a limited significance. It would be desirable for the patient to have a system that supports him or her in medication and treatment so that the patient is reminded of important scheduled times, so as to avoid forgetting to take important medications or keep doctor's appointments.

SUMMARY OF THE INVENTION

An object of the present invention is to provide a device for monitoring medication and treatment by patients on the basis of the patient card.

This object is inventively achieved in a device in the form of a pocket monitor having a clock or DCF-receiver, a plug-in receptacle for the patient card and a reader for treatment-relevant data as well as a display for displaying the readout information relating to the type and time of upcoming treatments and/or medication to be taken.

On the basis of the patient card, a second interface is thus inventively created for the possessor of the patient card that enables access only to part of the information stored on the patient card. A large amount of additional stored data is available only to the physician or health organization, who has a significantly more comprehensive card reading device available. The pocket monitor has no input possibility so that the stored patient data cannot be changed at all and can only be supplemented with additional data, e.g. the time that medication was administered.

In order to preclude misuse in the embodiment of the invention, the pocket monitor is provided with an identification circuit for enabling the display device. Such an identification circuit can contain either a fingerprint sensor or can be connected with a PIN code input device. In the case of a PIN code input device, instead of a keyboard for the input of the PIN code (as is normal), a cursor key is provided with which numbers can be selected on the display. Such a cursor key for the input of the PIN code can simultaneously control the executive sequencer of the display. By pressing the cursor key into the positions top, bottom, left or right, the corresponding areas of the screen can be selected and the display can also be "advanced" if, e.g. the taking of a medication requires the simultaneous taking of other medications that cannot be displayed on the screen all at once. In such a case, the design of the pocket monitor will naturally be such that the patient is automatically prompted to advance the screen, or the device automatically advances to a new display also needing attention at the same time after user acknowledgment of the current display, which the pocket monitor documents and stores.

Of specific significance for the inventive purpose of monitoring medication and patient treatment is an optical, acoustic, or tactile (vibrator for deaf patients) alarm that can be automatically activated via the patient card data, this automatically reminding the patient that a specific medication is due to be taken or that there is a specific appointment with the physician or therapist. In this time reminder function an advance notice can be provided—preferably via a program already permanently stored in the pocket monitor—so that the patient is reminded a day in advance or at least a few hours in advance of the respective treatment appointment. In a further embodiment of the invention, the alarm can have a wireless connection to an external alarm device so that the alarm that occurs when an alarm point is reached will also be transmitted to an external alarm device as a back-up. Thus it is assured that the alarm will be perceived, even if the patient is not carrying the pocket monitor on his or her person. The identification circuit operating on the basis of a PIN code or a fingerprint can be designed such that, in addition to the patient, specific caretakers also can have access to certain of the treatment data, of an appropriate scope. The detailed information about the appointments or medications only appears on the monitor display after this identification. The patient or caretaker acknowledges the administering of the medication, and the time can be noted automatically. In the simplest case a confirmation input key can be connected directly to the identification circuit, i.e. the patient or caretaker simply presses the fingerprint sensor or the cursor key in order to indicate that he or she has seen a display notice and taken action.

If a scheduled time is not met within the limits prescribed by the medication, then depending on the importance of a medication—either the dosage or the time interval can automatically be modified by a computer in the pocket monitor or an alarm can be given to visit a physician. These irregularities are also to be documented and stored in the pocket monitor, so that at the next appointment, the physician or caretaker has complete access to information regarding what the patient has done since the last treatment, or possibly has neglected to do.

The reminder regarding treatment appointments and the administering of specific medications is acknowledged by the patient in order to clear the alarm. Only the physician, therapist or caretaker, however, can record the beginning, type and end of the treatment since this data input requires a totally different device than the pocket monitor, that only represents a memory aid.

DESCRIPTION OF THE DRAWING

The single FIGURE shows an exemplary embodiment of a pocket monitor in accordance with the invention, with a patient card inserted therein.

DESCRIPTION OF THE PREFERRED EMBODIMENTS

The pocket monitor 1 has a plug-in receptacle for a patient card 2, into which the essential treatment data are entered by the physician or therapist. The patient card 2, of course, also contains purely administrative data and personal facts and information relating to invoicing the health insurance company. The data important for the inventive purpose of assisting the patient with respect to medication and treatment are, however, merely the data relating to the type and time of administering medication, the visits to the physician or therapist, or the like. The pocket monitor 1, preferably embodied as a flat case with a format (somewhat larger than a chip card) has a display 3, on which the patient can read the corresponding information. The pocket monitor 1 is provided with a reader 9 connected to a computer 8 so that the relevant treatment data are readout from the patient card 2 and—after the appropriate identification—are displayed on the display 3, also connected to the computer 8. In order to prevent misuse, an identification means is necessary for the possessor of the pocket monitor 1 or his or her caretaker. This identification means can be a fingerprint sensor 4 connected to the computer or a PIN code input. The PIN code input can ensue with the use of a cursor key 5 connected to the computer 8. Using the cursor key 5,—after activating the device 1 with a keystroke—the user can repeatedly successively select the respective PIN code numbers and thus identify himself or herself as the authorized user of the pocket monitor 1.

The pocket monitor 1 further has an alarm device that can also be an acoustic or tactile alarm indicator in addition to a blinking light 6 connected to the computer 8. When the patient card 2 is plugged in and the treatment-relevant data are thus automatically entered, the built-in computer 8 automatically determines the respective alarm times—which may be pre-dated—in order for a stored treatment appointment to be subsequently perceived by the patient. When the time arrives, e.g. for taking a medication as is shown on the monitor 3 of the FIGURE, the alarm indicator is triggered, and an external alarm device 7 which emits an optical, tactile or acoustic alarm signal also can be triggered via a wireless signal, as warranted. After such an alarm, the user must first activate the identification means, i.e. press, for example, the fingerprint sensor 4 shown in the exemplary embodiment, and subsequently the appropriate medication notice or the information regarding which treatment step the user must perform, e.g. whether as a diabetic an injection is needed, or the like appears on the display 3. The fingerprint sensor 4 thus also a servers as a confirmation input key, the actuation of which indicates the user has perceived the alarm. regarding which treatment step the user must perform, e.g. whether as a diabetic an injection is needed, or the like appears on the display 3.

Instead of a built-in clock, the pocket monitor 1 can have a DCF-receiver (real time receiver) so that it has access to the required time information that are indispensable to trigger an alarm corresponding to the data on patient card 2.

The invention is not limited to the exemplary embodiment presented. The structure and size of the pocket monitor and of its input and alarm means, as well as of the display can naturally vary as needed. The important innovation is that the inventive pocket monitor, in combination with a patient card, creates a second interface for the patient card data that reminds patients of important times limited to the treatment-relevant data. It is simultaneously precluded that the patient might intentionally or unintentionally change the patient card data, since the only access possibilities for him or her are the identification and confirmation at the display.

Although modifications and changes may be suggested by those skilled in the art, it is the intention of the inventors to embody within the patent warranted hereon all changes and modifications as reasonably and properly come within the scope of their contribution to the art.

We claim as our invention:

1. A device for monitoring medication and treatment of a patient, for use with a patient card containing physician-entered data, including comprehensive treatment-relevant data for a patient, said device comprising:

a pocket-sized housing containing no medication and having a receptacle adapted to receive a patient card;

a reader in said housing for reading only said treatment-relevant data from a patient card inserted in said receptacle;

a time source in said housing;

a computer in said housing connected to said -reader and to said time source for processing said comprehensive treatment-relevant data read by said reader;

a display screen externally disposed at said housing and connected to said reader and to said time source for displaying a reminder and a time, dependent on said processing of said comprehensive treatment-relevant data by said computer, of an upcoming treatment event; and an alarm contained in said housing and connected to said computer, said alarm being automatically triggered dependent on said processing of said comprehensive treatment-relevant data by said computer, and said alarm being selected from the group consisting of optical alarms, acoustic alarms and tactile alarms.

2. A device as claimed in claim 1 wherein said computer comprises an identification circuit and wherein said device further comprises an externally accessible element connected to said computer which must be actuated by a validated user to enable said display device.

3. A device as claimed in claim 2 wherein said externally accessible element is a fingerprint sensor.

4. A device as claimed in claim 2 wherein said externally accessible element is a PIN code input element.

5. A device as claimed in claim 4 wherein said PIN code input element is a cursor key disposed at an exterior of said housing for entering a PIN code having code elements, said code elements being displayed at said display screen dependent on actuation of said cursor key.

6. A device as claimed in claim 1 further comprising an external alarm in wireless communication with said computer, said external alarm also being automatically triggered dependent on said treatment-relevant data.

7. A device as claimed in claim 1 further comprising a confirmation input key which is externally accessible at said housing and which is connected to said computer for, when actuated, confirming acknowledgment of said treatment event.

8. A device as claimed in claim 7 wherein said treatment-relevant data include a timed sequence for administering a medication at a predetermined dosage, and wherein said computer automatically modifies at least one of a time and a dosage of said medication if no confirmation is received via said confirmation input key.

9. A device as claimed in claim 8 further comprising a memory accessible by said computer wherein any deviations from said sequence are stored as memory contents, said memory contents being subsequently readable.

10. A device as claimed in claim 8 further comprising an alarm unit in wireless communication with said computer, said alarm unit being disposed at a location remote from said housing and being triggered by a predetermined deviation from said sequence.

* * * * *